US010295448B2

(12) United States Patent
Verger et al.

(10) Patent No.: US 10,295,448 B2
(45) Date of Patent: May 21, 2019

(54) METHOD FOR THE QUALITY CONTROL OF A COMPONENT AT LEAST PARTIALLY MADE OF FILLED ELASTOMER

(71) Applicant: ANVIS SD FRANCE SAS, Decize (FR)

(72) Inventors: Serge Verger, La Machine (FR); Philippe Labaune, Yzeure (FR); Stephane Pannier, Moulins (FR); Thierry Charnotet, Saint Leger des Vignes (FR)

(73) Assignee: ANVIS SD FRANCE SAS, Decize (FR)

( * ) Notice: Subject to any disclaimer, the term of this patent is extended or adjusted under 35 U.S.C. 154(b) by 0 days.

(21) Appl. No.: 15/508,432

(22) PCT Filed: Sep. 4, 2015

(86) PCT No.: PCT/FR2015/052355
§ 371 (c)(1),
(2) Date: Mar. 2, 2017

(87) PCT Pub. No.: WO2016/038284
PCT Pub. Date: Mar. 17, 2016

(65) Prior Publication Data
US 2017/0261415 A1 Sep. 14, 2017

(30) Foreign Application Priority Data
Sep. 8, 2014 (FR) ...................................... 14 58411

(51) Int. Cl.
G01N 3/08 (2006.01)
G01N 3/32 (2006.01)
G01N 33/44 (2006.01)

(52) U.S. Cl.
CPC .................. *G01N 3/08* (2013.01); *G01N 3/32* (2013.01); *G01N 33/445* (2013.01); *G01N 2203/0094* (2013.01); *G01N 2203/0248* (2013.01)

(58) Field of Classification Search
CPC .......... G01N 3/08; G01N 3/32; G01N 33/445; G01N 2203/0094; G01N 2203/0248
(Continued)

(56) References Cited

U.S. PATENT DOCUMENTS 5,090,249 A * 2/1992 Bielewicz ................ G01N 3/08
                                                    73/822
6,778,914 B1 * 8/2004 Gillespie, Jr. ............ G01N 3/24
                                                    702/34
9,086,339 B2 * 7/2015 Lee ..................... G01R 31/2893

FOREIGN PATENT DOCUMENTS

FR       2925691 A1 *  6/2009  .............. G01N 3/32
WO  WO 2012080675 A1 *  6/2012  .............. G01N 3/08

OTHER PUBLICATIONS

Translation of FR 2925691 A1.*
(Continued)

*Primary Examiner* — Nathaniel T Woodward
(74) *Attorney, Agent, or Firm* — Young & Thompson

(57) ABSTRACT

Disclosed is a method for the quality control of a component at least partially made of elastomer, particularly for a joint, including: a) carrying out at least one accommodation cycle on the component, the accommodation cycle involving applying a progressive compression force to the component and progressively releasing the compression force without pulling; b) applying a progressive compression force to the component in quasi static state according to a given component deformation predetermined profile; c) measuring the deformation of the component and the compression force applied while the compression force is applied; d) determin-
(Continued)

ing the conformity of the component under a loading other than that of the compression force of step b) from the measurement of the deformation of the component and the compression force applied.

6 Claims, 4 Drawing Sheets

(58) Field of Classification Search
USPC .......................................................... 73/818
See application file for complete search history.

(56) References Cited

OTHER PUBLICATIONS

Translation of WO 2012080675 A1.*
Hu et al., Anelastic Behavior in Filled Elastomers Under Harmonic Loading Using Distributed Rate-Dependent Elasto-Slide Elements, chapter 13, 2012.*

* cited by examiner

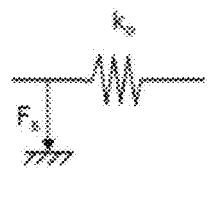
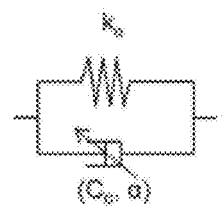
FIG. 6  FIG. 7
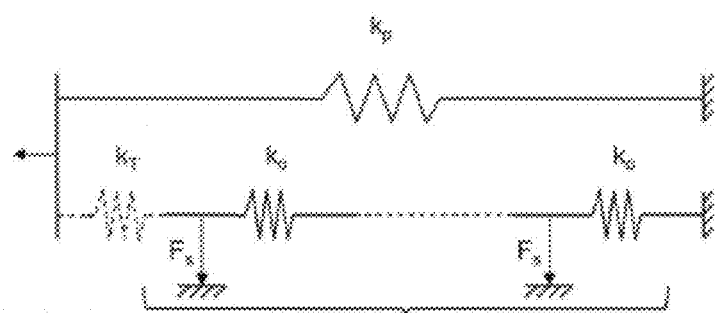
FIG. 8  N elementary cells
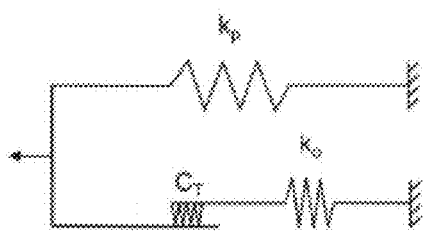
FIG. 9

METHOD FOR THE QUALITY CONTROL OF A COMPONENT AT LEAST PARTIALLY MADE OF FILLED ELASTOMER

TECHNICAL FIELD

The present invention relates to the technical field of methods for controlling the quality of a manufactured part. More precisely, the present invention relates to the technical field of methods for controlling the quality of a part at least partially made of filled elastomer, more particularly rubber.

STATE OF THE ART AND PROBLEMS FORMING THE BACKGROUND OF THE INVENTION

In the field of automobiles, for instance, controlling the quality of the manufactured part is particularly important, specifically for guaranteeing the quality/compliance of parts. Generally speaking, the production of parts at least partially made of filled elastomer must comply with particular specifications. Such specifications define characteristics that the part must comply with, such as the measurement of stiffness and of the phase so as to determine the loss angle for one or more mechanical stress(es).

The characteristics to be determined can be quasi-static characteristics, for instance. For this purpose, methods for determining such characteristics implement quasi-static regime testing, i.e. a stress is gradually applied onto the part to strain it. The quasi-static regime strain rate for the part is frequently of the order of 10 mm/min. Such methods generally use a traction-compression machine. In this type of machine, the part to be analyzed is fixed to a testing bench of the traction-compression machine and to a jack thereof, in order to study the behaviour of the part when submitted to an axial, or radial, conical or torsional stress. The jack is translatable, so that it can successively exert a compressive stress and a traction stress onto the part. The part strain (generally measured by the height of the part parallel to the direction of the applied stress) and the load applied are measured during the compression and traction phases in order to obtain a stress/strain transfer curve. Stiffness and damping are then determined from such measurements.

Because the part has to be fixed to elements of the traction-compression machine to apply the successive compressive and traction stresses, such methods require a relatively long time, generally above 10 min for each part measured. They additionally require trained personnel to correctly position the part in the machine and execute the test. Such methods thus cannot be implemented in a production line, in order to control the quality of all the parts which are manufactured for rate reasons, taking off samples being required to fix same to the traction-compression machine.

Additionally, the specifications also sometimes require checking the compliance with mechanical characteristics in dynamic mode for one or several strain(s) and one or more frequency(ies). Such measurements are conventionally made using servo-hydraulic traction-compression machines. Constraints are applied onto the part so that the strain curve of a control area of the part describes a sinusoid. The sinusoid frequency is preferably greater than or equal to 1 Hz. Fixing the part is thus all the more necessary since it must keep up with such strain frequency.

Servo-hydraulic traction-compression machines are rather expensive, too.

For information for the person having ordered the parts, or the final user, such dynamic characteristics sometimes have to be obtained for several frequencies and maximum strain. The steps mentioned above are thus repeated for several strains and several frequencies of application of different stresses.

Besides, all these methods consume larger amounts of energy, whether in terms of oil, electricity or water consumption. They also require trained operators and are noisy. The global cost of such measures is thus relatively high.

The document WO 2012/080675 relates to a method of driving in a quasi-static and modulated manner a test device for trials of mechanical loadings on a sample produced essentially from one or more materials exhibiting visco-elastoplastic behaviours, allowing the characterisation of the mechanical behaviour of the sample and the modeling of this behaviour. Such device comprises at least one mechanical loading assembly comprising at least one actuator making it possible to move a gripping means in axial displacement, along the axis of the sample held in the loading position. It consists essentially, on the basis of a computer, in controlling the or each actuator by sending and by injecting into the latter a signal representative of a speed setting or force setting, said signal being a sinusoidal modulated signal v(t) comprising a quasi-static component and a sinusoidal dynamic component. The document WO 2012/080675 also relates to a test device suitable for implementing the method.

The state of the art also comprises the document FR 2 925 691 and the articles by COVENEY V A et Al: « A triboelastic Model for the Cyclic Mechanical Behaviour of Filled Vulcanizates » and « Rate-dependent modeling of a highly filled vulcanizate » published in RUBBER CHEMISTRY AND TECHNOLOGY, AMERICAN SOCIETY, RUBBER DIVISION, US, respectively volume 68, n° 4, Sep. 1, 1995, pages 660-670 and volume 73, n° 4, Sep. 1, 2000, pages 565-577.

The need therefore exists for a method for characterizing the mechanical behaviour of parts subjected to stresses which can be directly implemented in a line of production of such parts.

SUMMARY OF THE INVENTION

The invention is summarized hereunder.

One of the aims of the invention is to remedy at least one of the drawbacks of the prior art as mentioned above.

More particularly, one aim of the invention is to provide a method for controlling the quality of a part at least partially made of filled elastomer, specifically rubber, which can be integrated in a part production line.

For this purpose, according to a first aspect, the invention provides for a method for controlling the quality of a part at least partially made of filled elastomer, more specifically for a joint, comprising:

a) the execution of at least one part accommodation cycle, with the accommodation cycle comprising the application of a gradual compressive force onto the part, and the gradual release of the compressive force with no traction;

b) the application of a gradual compressive force onto the part with a quasi-static regime according to a predetermined strain curve of the given part, with the gradual compressive force being applied until a maximum strain of the part is reached which occurs in a field where the relationship between the applied force and the strain is linear, c) the measurement of the part strain and the compressive force applied when applying the compressive force;

d) the determination of the part conformity with another stress than that of the compressive force of step b) from the measurement of the part strain and the applied compressive force; with the determination of the part conformity comprising the determination of the value of at least one intrinsic quasi-static mechanical characteristic of the part relative to the response thereof to a quasi-static stress, and to the comparison of such value with a predefined value; with the value of the mechanical characteristic being determined from a standard trioelastic stress/strain (STS) analytical model for parts of the same type as the part, and the measures obtained in step c).

Other optional but not restrictive characteristics are as follows.

The strain curve is advantageously quasi-linear.

Determining the part conformity may consist in determining the value of the quasi-static stiffness, respectively the value of the quasi-static phase, and in comparing same with a quasi-static stiffness, respectively quasi-static phase, predefined value.

The method may further comprise the determination of the value of an intrinsic quasi-static mechanical characteristic of the part relative to the response of the part to a dynamic stress, according to a predefined dynamic curve of the part strain, from the measurement of the part strain and the applied compressive force. In this case, it may also comprise determining the values of a dynamic stiffness and/or a dynamic phase from the quasi-static stiffness and/or the quasi-static phase thus determined. The given frequency is preferably greater than or equal to 1 Hz. The dynamic stiffness, respectively the dynamic phase may more particularly be obtained by multiplying the quasi-static stiffness, respectively, the quasi-static phase, by a coefficient based on the frequency and the filled elastomer which the part is at least partially made of.

According to a second aspect, the invention provides for a method for producing and controlling of a part at least partially made of filled elastomer comprising:

the manufacturing of a part at least partially made of filled elastomer;

the quality control of the part manufactured using the quality control method disclosed above.

According to a third aspect, the invention provides for a testing machine comprising a stress application cell for applying a compressive force onto a part at least partially made of filled elastomer, a control for controlling the stress application cell, a preferably programmable regulator, for regulating the control, a filler sensor for measuring the force applied, a position sensor for measuring the strain of the part and a computer connected to the filler sensor and to the position sensor, the regulator regulates the control to make the stress application cell execute a part accommodation cycle consisting in applying the gradual compressive force onto the part and the gradual release of the compressive force with no traction, the regulator regulating the control to also make the stress application cell apply a gradual compressive force onto the part for a quasi-static regime at a given part strain rate, the filler sensor and the position sensor being so regulated as to execute the measurement during the application of the compressive force by the stress application cell and to send such measurements to the computer, the computer is able to determine the conformity of the part from the measurement of the part strain and the applied compressive force, with the conformity being determined according to the Standard Triboelastic Solid model.

According to a fourth aspect, the invention provides for a production line of parts at least partially made of filled elastomer comprising:

a part manufacturing station;

a part quality control station comprising the machine of the third aspect and implementing the quality control method as disclosed above; and a switching station for separating the parts which do not meet the quality control criteria from the parts which meet the quality control criteria.

When compared to the prior art, the advantages of the invention are that the application of a compressive stress onto the part is required only to enable the quality control thereof. Besides, this further makes it possible to eliminate the necessity to fix the part in the testing machine. Consequently, the time required for determining the conformity of the part with the specifications is reduced, which enables implementing the unit quality control in the part production line.

Besides, the displacement of the part to the docking station can easily be automatized, for instance the docking station for making the measurements is on the part way along a conveying belt of a part production station toward a packaging or storing station. It is thus no longer required for the staff to be specially trained therefor, and the quality control is adapted to the parts production rate.

DESCRIPTION OF THE DRAWINGS

The figures in the drawings are described hereunder. Such figures are illustrative and not restrictive ones, and among these:

FIG. 6 is a schematic representation of an elementary cell used in a STS model for the part partially made of filled elastomer;

FIG. 7 is a schematic representation of an elementary cell used in a RT (rate-depending triboelastic) model for the part partially made of filled elastomer;

FIG. 8 is a schematic representation of the part partially made of filled elastomer used in a STS model with N elementary cells;

FIG. 9 is a schematic representation of the STS model equivalent to FIG. 8 with $C_T=2K_T F_S$;

DISCLOSURE OF THE INVENTION

Figure 1:
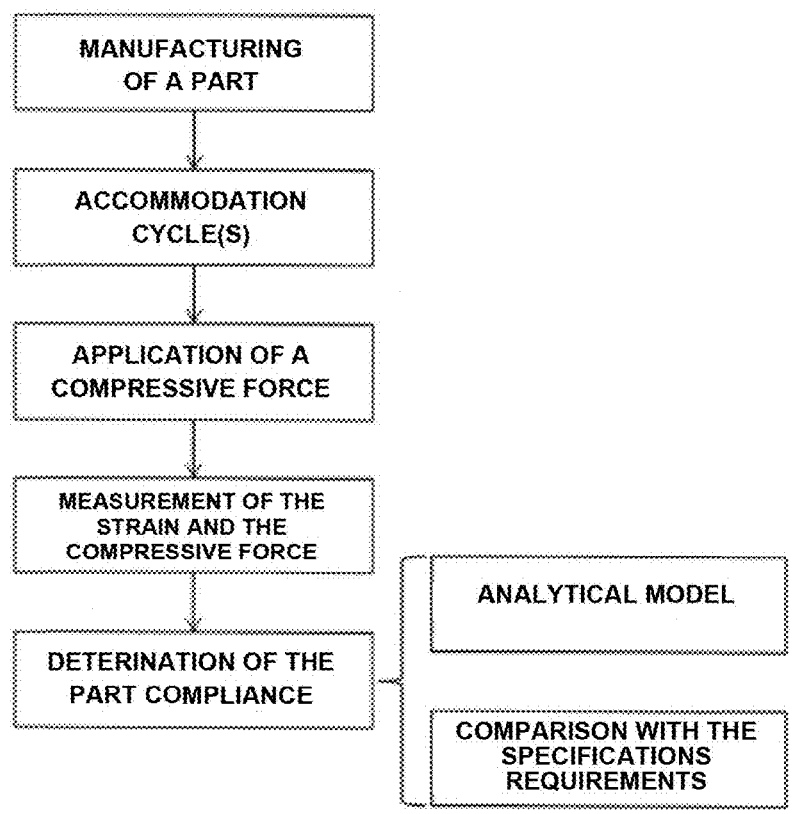
FIG. 1 is a flowchart illustrating the steps of the method according to the invention.

A detailed exposure of several embodiments of the invention illustrated by examples and referring to the drawings is given hereunder.

First a method for controlling the quality of a part at least partially made of filled elastomer according to the invention is disclosed hereunder while referring to FIGS. 1 to 8. Such method more particularly enables the quality control of parts at least partially made of filled elastomer, for instance rubber, such as typically parts for cars, trains, etc.

«Filled elastomer» means, within the scope of the present invention polymer filled with reinforcing fillers, for example carbon black or a mixture of silica and silane, having elastic properties obtained after crosslinking, for example, polybutadiene, styrene-butadiene copolymer, polyisobutylene (or still isobutylene-isoprene rubber, also called butyl rubber), etc.

"Rubber" means both natural rubber and synthetic rubber. Natural rubber is manufactured from latex extracted from plants such as, for instance, the rubber tree (*Hevea brasiliensis*) and the rubber plant (*Ficus elastica*). Synthetic rubber is manufactured from monomers derived from fossil fuels.

«Rubber» also means the mixtures of at least one of natural rubber and synthetic rubber, filled natural rubber, filled synthetic rubber, filled mixtures, as well as the composites mainly consisting of filled natural and/or synthetic rubber.

Composite means materials consisting of at least two materials having significantly different physical and/or chemical properties which are so combined that the composite obtained has characteristics different from the materials it is made of (called components). The components are not mixed and remain separate from each other, while being in close contact together, i.e. they can be separated with difficulty only.

Figure 2:
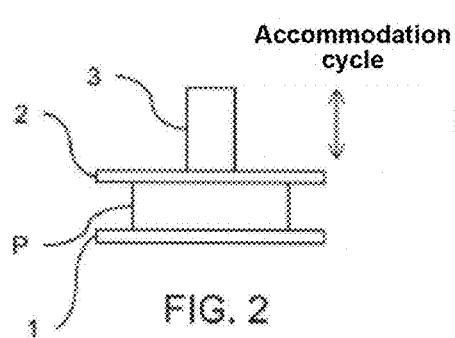
FIG. 2 is a schematic view of the step of accommodation of the method of FIG. 1, wherein a part made of filled elastomer P and two metallic frames 1, 2, placed but not fixed in a recess in the testing machine specially provided for this purpose, and a jack 3 for applying a compressive force can be seen.
Figure 3:
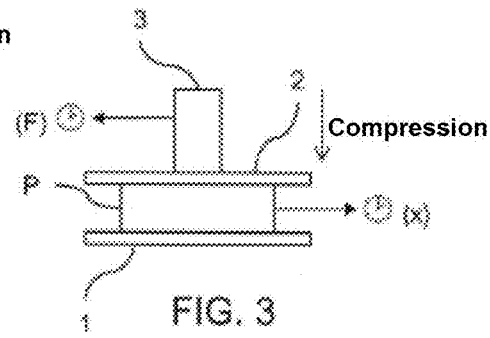
FIG. 3 is a schematic view of the step of applying a gradual compressive force and the step of measuring the applied compressive force and the strain of the method of FIG. 1, wherein a part made of filled elastomer P and two metallic frames 1, 2, placed but not fixed in a recess in the testing machine specially provided for this purpose, and a jack 3 for applying a compressive force can be seen.
Figure 4:
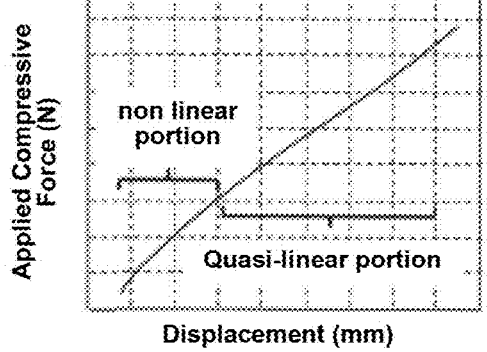
FIG. 4 is an exemplary graphic representation of the measurements made, which shows a graph illustrating the compressive force applied vs the position.

The method comprises:

a) the execution of at least one part accommodation cycle, with the accommodation cycle comprising the application of a gradual compressive force onto the part, and the gradual release of the compressive force with no traction (FIG. 1);

b) the application of a gradual compressive force onto the part with a quasi-static regime according to a predetermined strain curve of the given part (FIG. 2);

c) the measurement of the part strain and the compressive force applied when applying the compressive force (FIG. 3);

d) the determination of the part conformity with another stress than that of the compressive force of step b) from the measurement of the part strain and the applied compressive force, with the conformity being determined according to the standard triboelastic solid model.

This method thus requires no traction stress. This eliminates the necessity to fix the part in the testing machine.

The accommodation cycle makes it possible to free from the Mullins effect. The Mullins effect is a particular aspect of the mechanical response of elastomers, wherein the stress/strain curve depends on the maximum filler previously applied. It causes a loss in rigidity for strains applied after a first stress.

Although only one accommodation cycle is necessary, it is sometimes preferable to execute two or three accommodation cycles, or even more, in order to obtain a better stabilization of the elastomer prior to measurements.

«Part strain» in the present document means the strain which occurs in a control region of the part. The control region is the place where the force is applied onto the part. The person skilled in the art will know how to determine the control region and thus to measure the part strain.

«Strain curve» in the whole present document means a temporary evolution of the part strain. The derivative of the strain curve gives the strain rate.

The strain curve is advantageously quasi-linear. «Quasi-linear», in the whole of the present invention means a strain rate which varies within ±5% of a chosen value, or is even constant at the chosen value (linear curve). The part strain rate, in absolute value, during the compression and the release executed in step a) must be higher than the part strain rate during the compression executed in step b) to optimize the time of the accommodation cycle.

Alternately, the part strain rate, in absolute value, during the compression and the release executed in step a) and that of the compression executed in step b) may be the same.

Besides, the strain relative to 0, during step a) must preferably be greater than the one obtained during step b). In practice, it may be equal to the maximum value for which the compliance of the part must be determined.

In another example, the strain curve may also be partly linear, which means that it shows portions where it is linear and the strain rate changes at the intersection of such portions. The strain curve may also be bent, periodical (triangular or sinusoidal, etc.), etc.

«Gradual», means that the compressive force applied is low at the start and that it increases slowly, preferably continuously, although within a very short time, or that the force applied is released slowly, preferably continuously.

The quasi-static regime refers to a regime wherein, although the compressive force applied changes and the part strains all along the application of the compressive force, the behaviour of the part at each moment as considered separately from the compression is close to a static behaviour. This means that the physical phenomena which occur during a dynamic regime only are minimized.

The quasi-static regime is preferably characterized by a time of application of the compressive force of less than one second, preferably at a part strain rate, defined in the whole of the present document in the direction of the applied compressive force of less than 1 mm/s, preferably above 10 mm/min.

The compressive force is advantageously applied until it reaches a maximum strain of the part within a field where the relationship between the applied force and the strain of the part is linear and outside the limit between the non-linear field and the linear field. As a matter of fact, and as mentioned above, when the maximum force applied is below the maximum force previously applied, the behaviour of the filled elastomer is firstly non-linear until the force applied reaches a given value, from which the behaviour of the filled elastomer becomes linear.

Generally speaking, upon completion of the accommodation cycle(s), applying the compressive force onto the part without releasing it and making only one series of measurements upon applying the compressive force is sufficient. However, release can also occur, without any traction, further to the application of the compressive force forming a measurement cycle, with the measurement then being made all through the cycle. Several measuring cycles can thus be executed, with the measurement of the applied compressive force and part strain being made during such cycles.

A graph can then be drawn from the measurements of the applied force and the part strain in order to obtain a visual representation of the part behaviour relative to the applied force, although the drawing thereof is not required for the rest of the method. Strain is currently represented on the x axis and the applied force on the y axis. A first portion of a non-linear curve will then be observed until strain (and thus the applied compressive force, too) reaches a limit value. If the compressive force continues increasing, a second portion of a linear curve will be observed. The equation of such a curve portion is thus as follows:

$$F(x)=p \cdot x+a;$$

with $F(x)$ being the applied compressive force, x the strain, p the curve slope, which may vary depending on x by ±5%, both as regards the abscissae and the ordinate.

The words «other stress» refer to a mechanical stress different from the one applied in step b). The present method thus makes it possible to determine the compliance of the part with a stress which has not been applied thereto.

The other stress may be the application of a compressive force to a strain curve of the part which is different from the one used in step b).

The other stress may also be a dynamic stress, as opposed to the compressive force applied in step b), which is a quasi-static stress. The dynamic stress is generally the repeated application of a compressive force and a traction force. Such repeated application is generally periodic, for example sinusoidal or triangular, and thus has a given frequency.

Determining the compliance of the part consists in checking that the technical properties of the part meet the requirements, for instance those mentioned in specifications. It advantageously comprises the determination of the value of at least one intrinsic quasi-static mechanical characteristic, preferably two intrinsic quasi-static mechanical characteristics of the part relative to the response thereof to a quasi-static stress, and the comparison of such value, preferably such values, with a predetermined value specifically representing the requirements of specifications.

When the values of two intrinsic quasi-static mechanical characteristics are determined, such two mechanical characteristics are advantageously the stiffness and the phase in stationary regime, hereafter called quasi-static stiffness and quasi-static phase.

Determining the mechanical characteristic, specifically the quasi-static stiffness and the quasi-static phase, executed with the method of the invention gives values which are very close to the ones which would have been obtained using more conventional methods, (refer to the example hereunder), such as tests carried out using a traction-compression machine, for instance. As a matter of fact, the same results can be obtained for the quasi-static stiffness and the quasi-static phase as those with a method using a traction-compression machine, wherein a cycle of application of a compressive force and a traction force is repeated several times (with a strain rate generally below 10 mm/min) and wherein the force applied and the strain of the part are measured.

The mechanical characteristic, specifically the quasi-static stiffness and/or the quasi-static phase, is for instance determined from the same stress/strain analytical model for parts like the part, and the measurements obtained in step c).

The stress/strain analytical model optionally makes it possible to obtain a transfer curve representing the estimated compressive force required to be applied according to the strain. Such transfer curve corresponds to the one which would have been obtained in quasi-static mode with conventional methods, which is obtained from the measurements made. Such transfer curve generally discloses an hysteresis cycle, i.e. closed contour, generally symmetrical relative to the origin, i.e. the (0;0) point. The transfer curve is not necessarily drawn or displayed.

One exemplary strain analytical model is the standard triboelastic solid model (or STS model). Such model is an analytical model disclosed in the document entitled «A triboelastic model for the cyclic mechanical behavior of filled vulcanizates» (in French «Un modèle triboélastique pour le comportement mécanique cyclique des vulcanisés chargés) by V. A. Coveney et al., in Rubber Chemistry and Technology: September 1995, Vol. 68, No. 4, pp. 660-670.

Such model is based on the series combination of one element having a purely elastic behaviour (represented by a spring) and one element having a tribological behaviour (represented by a solid friction element). The result of the linear superposition of both elements is the elementary cell. FIG. 6 represents an elementary cell with a spring having a stiffness $k_0$ and a solid friction element having a threshold force $F_s$. The value of the threshold force $F_s$ is a limit value, which means that a force applied to the solid friction element having a value above the limit value translates the friction element and that a force applied to the solid friction element having a value under the limit value does not move the solid friction element.

The model can be perfected by using a series combination of a plurality of elementary cells. In this case, an additional purely elastic element is required and is positioned parallel with the series combination of elementary cells. Such additional purely elastic element, represented by a spring having a stiffness $k_p$, represents a global elastic stiffness. FIG. 8 represents such an arrangement of the mentioned elements (without the spring $k_T$ in doted lines).

The model can still be perfected by adding another purely elastic element positioned in series with the series combination of elementary cells. Such additional purely elastic element, represented by a spring having a stiffness $k_T$, represents an additional stiffness with a small displacement (refer to FIG. 8).

The model can still be perfected by adding Maxwell cells to modelize the visco-elastic behaviour.

Other models are still possible, such as for instance the rate-dependent triboelastic model (or RT model) presented in the article «Rate-dependent modeling of a highly filled vulcanizate» (in French «Modélisation dépendante de la vitesse d'un vulcanisé hautement chargé» ), by V. A. Coveney and D. E. Johnson, in Rubber Chemistry and Technology: September 2000, Vol. 73, No. 4, pp. 565-577. In this model, the solid friction element has been replaced by a friction element depending on the rate to form the elementary cell (refer to FIG. 7).

Generally, the analytical model provides an equation disclosing the applied force F according to the strain x, the maximum values of the applied force ($F_m$) and the strain ($X_m$), as well as analytical parameters such as $k_P$, $C_T$ and $K_O$ . . . . The analytical model provides the general form of the equation only. The analytical parameters then have to be determined.

Thanks to the STS model, the following equation, for instance, can be determined and discloses the behaviour of the part when submitted to a compressive stress:

$$F = k_P \cdot x + F_m + \frac{\lambda \cdot C_T}{2K_0} \cdot \text{sgn}(x - X_m) \cdot \left( \sqrt{1 + 4k_0^2 \cdot \frac{|x - X_m|}{\lambda \cdot C_T}} - 1 \right),$$

With λ=1 before the first extremum and 2 afterwards.

The analytical parameters can be determined ($K_P$, $C_T$ and $K_O$) from the measurements executed during step c) (refer to FIG. 4) and the analytical model.

Figure 5:
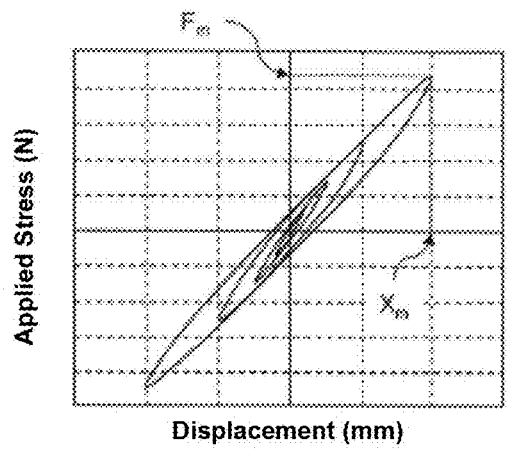
FIG. 5 is an example of the result which can be obtained with the method of FIG. 1, and shows the estimated stress the part is subjected to according to the position shown of the conventionally used method, to show the result obtained with a conventional method wherein the part is submitted to several cycles comprising the application of a compressive force and the application of a traction force onto the part for several traction/compression values.

The equation provided by the analytical model can thus be completed for the given part and the quasi-static behaviour thereof under various traction/compression conditions can be deduced from the completed equation (refer to FIG. 5).

The quasi-static stiffness is obtained using the following formula:

$$k_s = \frac{F_2 - F_1}{X_2 - X_1},$$

where $k_s$ is the quasi-static stiffness, $F_1$ and $F_2$ two values of the force applied to a quasi-linear zone of the curves obtained using the complete analytical model and X1 and X2, the corresponding strains.

The quasi-static phase is calculated from the area inside the corresponding curve.

The value of the quasi-static stiffness, respectively of the quasi-static phase, is compared with a value of the predetermined quasi-static stiffness, respectively that of the quasi-static phase. If the value of the quasi-static stiffness, respectively that of the quasi-static phase, is equal to the predetermined value of the quasi-static stiffness, respectively that of the quasi-static phase, within a tolerance considered as acceptable in the specifications, then the part meets the quasi-static stiffness, respectively quasi-static phase conditions, and is declared compliant. If not so, the part is declared non-compliant and disposed of.

In the case where both values are used for determining the compliance of the part, the part must meet the predefined criteria for both values in order to be declared compliant, otherwise it is declared non-compliant.

The determination of the part compliance advantageously comprises the determination of the value of a dynamic stiffness corresponding to the one which would have been determined when applying onto the part a compressive force and a traction force repeatedly, specifically periodically, with a frequency f. In this case, the value of the dynamic stiffness is compared with a predetermined value of the dynamic stiffness. If the dynamic stiffness is equal to the value of the predetermined dynamic stiffness, within a tolerance considered as acceptable in the specifications, then the part meets the dynamic stiffness conditions. The part is declared compliant if it meets all the fixed conditions, otherwise it is declared non-compliant.

The dynamic stiffness with the frequency corresponding to the strain curve used in step b) is obtained with the following formula:

$$k_d = \frac{F_m}{X_m},$$

where $k_d$ is the dynamic stiffness at such frequency, $F_m$ the maximum force applied and $X_m$ the corresponding strain.

The strain curve used in step b) is preferably quasi-linear and the frequency f complies with the following formula:

$$f = \frac{v}{A};$$

with v the strain rate used in step b) and A the maximum compressive force applied in step b).

Generally, according to the manufactured part, the specifications therefor require a dynamic characterization of the part. Determining the value of the intrinsic dynamic mechanical characteristic of the part relative to the response thereof to a dynamic stress according to a predefined dynamic curve for the part strain is thus required. Such determination is obtained from the measurement of the part strain and the compressive force applied.

When the determined quasi-static mechanical characteristics are the quasi-static stiffness and/or the quasi-static phase, the dynamic mechanical characteristic is preferably the dynamic stiffness and/or the dynamic phase corresponding to parameters representative of the mechanical response of the part to a stress of the part at a given frequency. Both are determined from the quasi-static stiffness and/or quasi-static phase.

For instance, these can be obtained with the present method using hardening coefficients according to frequency. Such coefficients represent the noted phenomenon of hardening of filled elastomers when the latter are submitted to compressive and traction forces at high frequencies.

«Frequency» which is used here, refers to the fact that, in conventional methods, the part is submitted to repeated cycles comprising the application of a compressive force and a traction force. Such repetition results in a sinusoidal strain of the part at a given frequency. The present method thus makes it possible to determine the dynamic stiffness and the dynamic phase which would have been obtained using the conventional methods at a given frequency. Such frequencies generally range from 1 Hz to 300 Hz.

The dynamic stiffness $k_f$ at a frequency f is given by the following formula:

$$k_f = C_{k,f} k_d;$$

with $k_d$ being the dynamic stiffness obtained above and $C_{k,f}$ the hardening coefficient according to the frequency for the stiffness.

The dynamic stiffness $\varphi_k$ at a frequency f is given by the following formula:

$$\varphi_f = C_{\varphi,k} \cdot \varphi;$$

with $\varphi_k$ being the phase obtained using the method of the invention and $C_{\varphi,f}$ the hardening coefficient according to the frequency for the phase.

The hardening coefficients according to the frequency depend on the rubber used and the strain curve used in step b). Such coefficients can be determined from conventional dynamic measurements or an internal elastomer data base. They can also be obtained during the measurement using other methods (for instance creep or relaxation); such methods however take more time.

The quality control method disclosed above can be integrated in a method for manufacturing and controlling a part at least partially made of filled elastomer, specifically rubber. The method comprises:

the manufacturing of a part at least partially made of filled elastomer; and the quality control of the part manufactured using the quality control method disclosed above.

Figure 10:
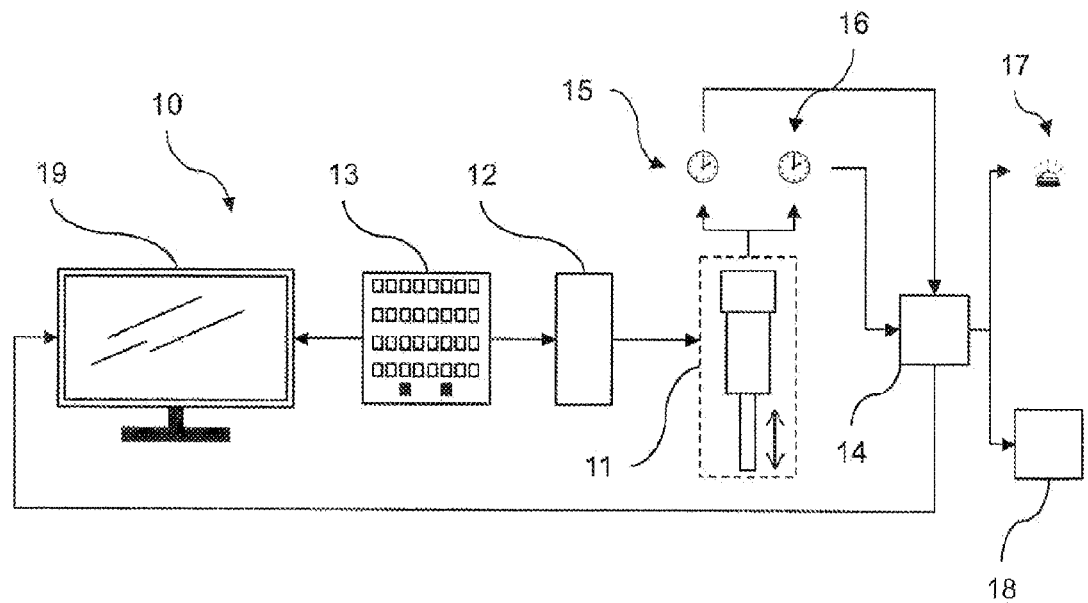
FIG. 10 is a schematic representation of a testing machine specifically dedicated to the method of the invention.

An exemplary testing machine specifically dedicated to the implementation of the method disclosed above is described while referring to FIG. 10.

The testing machine 10 comprises a cell 11 for applying stresses in order to apply the compressive force onto the part, a control 12 for controlling the stress application cell 11, a preferably programmable regulator 13, for regulating the control 12, a computer 14, a filler sensor 15 for measuring the applied force and a position sensor 16 for measuring the part strain.

The filler sensor 15 and the position sensor 16 are connected on one side to the stress application cell 11 and on the other side, to the computer 14.

The regulator 13 regulates the control 12 to make the stress application cell 11 execute a part accommodation cycle consisting in applying the gradual compressive force onto the part and the gradual release of the compressive force with no traction.

The regulator 13 regulates the control 12 to also make the stress application cell 11 apply a gradual compressive force onto the part for a quasi-static regime at a given part strain rate.

The filler sensor 15 and the position sensor 16 are so regulated as to execute the measurement during the application of the compressive force by the stress application cell 11 and to send such measurements to the computer 14.

The computer 14 is able to determine the compliance of the part from the measurement of the part strain and the compressive force applied.

The application cell 11 preferably comprises an electric jack.

The testing machine 10 may also comprise a signaler 17 connected to the computer 14 in order to emit a signal when it has been determined that the part did not meet the quality requirements. The signal may be visual, such as a light, or a noise, such as the emission of a sound.

The testing machine 10 may further or alternately comprise a switch 18 connected to the computer for directing the part detected as faulty toward a waste tank.

The testing machine 10 may still comprise a display 19, such as the screen of a computer, a tablet, a LCD screen, so connected to the computer 14 as to display the characteristics of the part which have been measured. The display 19 may also display other information such as the batch number, the compliance or non-compliance with the specifications, etc. The display 19 may also be connected to the regulator 13 in order to facilitate the regulation of the control.

The testing machine 10 is adapted to implement the quality control method disclosed above.

Figure 11:
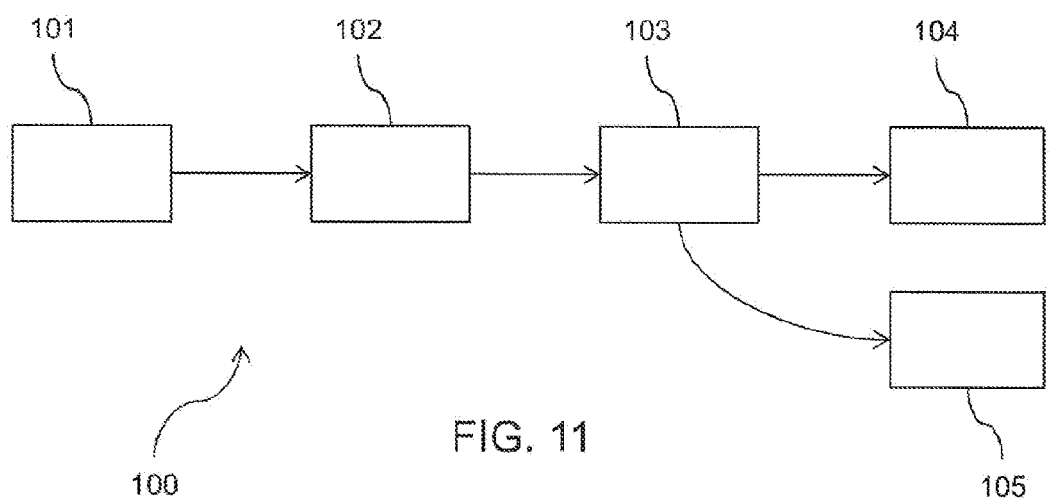
FIG. 11 is a schematic representation of a manufacturing line and parts partially made of filled elastomer according to the invention comprising the testing machine of FIG. 10 in a quality control station.

Such testing machine 10 can be integrated in a production line 100 of parts at least partially made of filled elastomer (FIG. 11), further comprising:
- a part manufacturing station 101;
- a part quality control station 102 comprising the testing machine as disclosed above 10; and
- a switching station 103 for separating the parts which do not meet the quality control criteria from the parts which meet the quality control criteria.

Optionally, the manufacturing line 100 may also comprise a collecting tank 104 intended to receive the parts having passed the quality control and a waste tank 105 intended to receive the parts not having passed the quality control.

Example 1

The present method has been tested on a soft portion of 10 reference parts made of rubber. Such parts are joints such as shock absorber brackets, i.e. flexible joints. 1 accommodation cycle has been executed. Further to the accommodation cycle, the parts have been submitted to a gradual compressive force up to a maximum of 780N. The strain rate was 1 mm/s.

The STS model disclosed above has been used to determine the stiffness and the phase of the part.

The results of table 1 hereunder have been obtained. Such results are compared with the results obtained with conventional methods, with a stationary and dynamic regime using a servo-hydraulic machine.

TABLE 1

|  | Example 1 | Conventional methods | Differences (as a percentage) |
|---|---|---|---|
| Stiffness (N/mm) | | | |
| Quasi-static, ±1.00 mm* | 445 | 453 | 1.7 |
| Dynamic, ±1.00 mm, 1 Hz* | 479 | 477 | 0.5 |
| Dynamic, ±1.00 mm, 15 Hz* | 497 | 500 | 0.6 |
| Dynamic, ±0.10 mm, 150 Hz* | 967 | 936 | 3.3 |

|  | Phase (degrees) | | Differences in degrees |
|---|---|---|---|
| ±1.00 mm, 1 Hz* | 7.95 | 7.8 | 0.15 |
| ±1.00, 15 Hz | 9.05 | 9 | 0.05 |

Data marked with an asterisk are sufficient for the quality control.

In the field of rubber mechanical characterization, the measurement error in absolute value generally amounts to about 5%. A determination with a difference of less than 5% with that of conventional methods is thus very satisfactory.

Example 2

The present method has been tested on a soft portion of 3 reference parts made of rubber. Such parts are joints such as cylindrical elastic joints, i.e. rigid joints. 1 accommodation cycle has been executed. Further to the accommodation cycle, the parts have been submitted to a gradual compressive force up to a maximum of 6,500N. The strain rate is 0.5 mm/s.

The STS model disclosed above has been used to determine the stiffness and the phase of the part.

The results of table 2 hereunder have been obtained. Such results are compared with the results obtained with conventional methods, with a stationary and dynamic regime using a servo-hydraulic machine.

TABLE 2

|  | Example 2 | Conventional methods | Differences (as a percentage) |
|---|---|---|---|
| Stiffness | | | |
| Quasi-static, ±0.30 mm* | 15813 | 15968 | 0.97 |
| Dynamic, ±0.10 mm, 1 Hz* | 21137 | 21233 | 0.45 |
| Dynamic, ±0.01 mm, 100 Hz* | 35661 | 35453 | 0.59 |

|  | Phase | | Differences in degrees |
|---|---|---|---|
| ±0.10 mm, 1 Hz* | 7.58 | 6.86 | 0.71 |

Data marked with an asterisk are sufficient for the quality control.

In the field of rubber mechanical characterization, the measurement error in absolute value generally amounts to about 5%. A determination with a difference of less than 5% with that of conventional methods is thus very satisfactory.

The invention claimed is:

1. A testing machine (10) for testing an elastic part made of filled elastomer (P) and two metallic frames (1,2), said testing machine (10) comprising:
   a recess wherein the part is positioned for testing;
   a stress application cell (11), which includes an electric jack (3) configured to apply a compressive force onto the part thereby to cause a strain to be applied to the part;
   a control (12) that controls the stress application cell (11);
   a programmable regulator (13) that regulates the control (12);
   a filler sensor (15) connected to the stress application cell (11) that measures the force applied by the application cell (11) when the stress application cell (11) applies the compressive force onto the part;
   a position sensor (16) connected to the stress application cell (11) that measures a strain upon the part when the stress application cell (11) applies the compressive force onto the part,
   a computer (14), in communication with the filler sensor (15) and the position sensor (16), the computer configured to determine a conformity of the part from the measured strain and the measured compressive force,
   wherein the part is positioned in the recess but not fixed within the recess,
   wherein the regulator (13) regulates the control (12) to cause the stress application cell (11) to execute a part accommodation cycle consisting of a gradual first application of compressive force onto the part and a subsequent gradual release of the compressive force with no traction,
   wherein the regulator (13) regulates the control (12) to cause the stress application cell (11) to execute a gradual second application of compressive force onto the part with a quasi-static regime until a maximum strain of the part is reached,
   wherein the maximum strain of the part occurs in a field where the relationship between the applied force and the strain is linear,
   wherein the computer (14) is configured to determine from the measured strain and the measured compressive force at least one mechanical characteristic of the part selected from the group consisting of quasi-static stiffness and the quasi-static phase, and to determine therefrom the conformity of the part according to the Standard Triboelastic Solid (STS) model, and
   wherein the testing machine is configured to operate as part of a production line and enable a switching station to separate parts which do not meet the quality control criteria from the parts which meet the quality control criteria.

2. A method for non-destructive testing a quality of an elastic part made of filled elastomer (P) and two metallic frames (1,2), said method comprising:
   receiving, in a recess of a testing machine the part to be tested, the part being positioned in the recess but not fixed within the recess;
   applying, via a stress application cell (11) that includes an electric jack (3), a part accommodation cycle consisting in a gradual first application of compressive force by the jack (3) onto the part, and a subsequent gradual release of the compressive force with no traction;
   applying, via the stress application cell, a gradual second application of compressive force onto the part with a quasi-static regime until a maximum strain of the part is reached, where the maximum strain of the part occurs in a field where the relationship between the applied force and the strain is linear;
   measuring, via a filler sensor (15) connected to the stress application cell (11) the force applied by the application cell (11) when the stress application cell (11) applies the compressive force onto the part;
   measuring, via a position sensor (16) connected to the stress application cell (11), a strain upon the part when the stress application cell (11) applies the compressive force onto the part;
   determining, via a computer in communication with the filler sensor (15) and the position sensor (16), a conformity of the part from the measured strain and the measured compressive force,
   wherein the computer (14) is configured to determine from the measured strain and the measured compressive force at least one mechanical characteristic of the part selected from the group consisting of quasi-static stiffness and the quasi-static phase, and
   to determine therefrom the conformity of the part according to the Standard Triboelastic Solid (STS) model.

3. The method according to claim 2, wherein a switching station (103) is caused to separate the part upon a determination that the part does not meet the quality control criteria.

4. A method for producing and controlling an elastic parts made of filled elastomer (P) and two metallic frames (1,2), the method comprising:
   receiving a series of said parts at a testing machine located along a production line for producing said parts,
   where for each part received at the testing machine,
     the part is placed, but not fixed, in a recess of the testing machine,
     a stress application cell (11) of the testing machine, including an electric jack (3), executes an accommodation cycle consisting in a gradual first application of compressive force by the jack (3) onto the part, and a subsequent gradual release of the compressive force with no traction,
     a stress application cell (11) of the testing machine executes a gradual second application of compressive force onto the part with a quasi-static regime until a maximum strain of the part is reached, where the maximum strain of the part occurs in a field where the relationship between the applied force and the strain is linear,
     a filler sensor (15) connected to the stress application cell (11) measures the force applied by the application cell (11) when the stress application cell (11) applies the compressive force onto the part,
     a position sensor (16) connected to the stress application cell (11) measures a strain upon the part when the stress application cell (11) applies the compressive force onto the part, and
     a computer in communication with the filler sensor (15) and the position sensor (16), a conformity of the part from the measured strain and the measured compressive force,
     the computer (14) configured to determine from the measured strain and the measured compressive force at least one mechanical characteristic of the part selected from the group consisting of quasi-static stiffness and the quasi-static phase, and to determine therefrom the conformity of the part according to the Standard Triboelastic Solid (STS) model; and causing a switching station, located along the production line, to separate parts which do not meet the quality control criteria from parts which meet the quality control criteria.

5. The method according to claim 4, wherein the parts which do not meet the quality control criteria are received in a waste tank (105), and the parts which meet the quality control criteria are received in a collecting tank (104).

6. A production of line for producing and controlling an elastic parts made of filled elastomer (P) and two metallic frames (1,2), wherein the production line implements the method of claim 4.

* * * * *